US00PP08440P

United States Patent [19]

Yoshida et al.

[11] Patent Number: Plant 8,440

[45] Date of Patent: Nov. 2, 1993

[54] APPLE TREE "KIZASHI"

[75] Inventors: Yoshio Yoshida, Ebetsu; Tadayuki Haniuda, Suzaka; Shichiro Tsuchiya, Tsukuba; Tetsuo Masuda, Naka; Hideo Bessho, Morioka; Tetsuro Sanada, Tsukuba; Sadao Komori, Morioka, all of Japan; Donald W. McKenzie, deceased, late of Havelock North, New Zealand, by Joy McKenzie, legal representative

[73] Assignee: Fruit Tree Research Station Ministry of Agriculture, Forestry and Fisheries, Tsukuba, Japan

[21] Appl. No.: 840,072

[22] Filed: Feb. 25, 1992

[51] Int. Cl.[5] ..... A01H 5/00

[52] U.S. Cl. ..... Plt./34.1

[58] Field of Search ..... Plt. 34.1

[56] References Cited

PUBLICATIONS

Bulletin of the Fruit Tree Research Station (Ministry of Agriculture, Forestry and Fisheries), No. 20, pp. 25–40, 1991.

*Primary Examiner*—James R. Feyrer

*Attorney, Agent, or Firm*—Armstrong, Westerman, Hattori, McLeland & Naughton

[57] ABSTRACT

Disclosed is an apple tree having a strong vigor, long and narrow leaves, and bearing a slightly small fruit maturing earlier than "Tsugaru". The fruit has a conical to rounded-conical shape, and a deep red to deep reddish orange (ISCC - NBS) skin. The flesh of the fruit is yellowish (ISCC - NBS) white, juicy and has a moderate texture, and further, has a moderate sweet and sour taste. The fruit of the present apple trees ripen for eating and can be picked earlier than other early maturing varieties, thereby providing the fruit with an excellent market value, in particular, in mid-summer.

6 Drawing Sheets

BACKGROUND OF THE VARIETY

The present invention relates to a new and distinct variety of apple tree constituting an early maturing apple cultivar, and more particularly, relates to an apple variety suitable for an earlier shipping than "Tsugaru" and "Sansa".

Until now, there were no good early maturing varieties in Japan, and thus the "Tsugaru" and "Sansa" have been treated as an early maturing variety, although they are not correctly an early maturing variety. As a result, in the warm apple-growing districts of Japan immature fruit of the "Tsugaru" and "Sansa" have been supplied to consumers at the earliest picking time, but this fruit did not have a quality satisfactory to the consumers.

Accordingly, the present breeders have conducted numerous experimental crosses, to thus provide an apple variety having earlier maturing fruit than "Tsugaru" and "Sansa", and having a high quality that will increase the consumption of the fruit. The tree of this invention makes available to apple growers an added option by providing a tree which is ripe for harvest prior to the seasons of later maturing varieties, thereby not competing with such varieties for labor at the time of harvest. Namely, the purpose of the invention is to provide a new and distinct variety of apple tree suitable for an earlier shipping of the fruit, compared with the fruit of the "Tsugaru" and "Sansa".

ORIGIN AND ASEXUAL REPRODUCTION OF THE VARIETY

To accomplish this purpose, the breeders crossed "Cox's Orange Pippin", which is a main cultivar in England, with "Starking Delicious" or "Golden Delicious", etc., to obtain a new type of apple tree bearing fruit that has a good flavor, storage ability, and a moderately sweet and sour taste. Nevertheless, the breeders could obtain only one individual breeding mother plant by crossing "Starking Delicious" and "Cox's Orange Pippin". Accordingly, the breeders selected a "Gala" as a parent for a breeding, which is good apple variety chosen from a cross between "Cox's Orange Pippin" and "Starking Delicious", and "Golden Delicious" in New Zealand.

Specifically, Dr. McKenzie crossed "Fuji" pollen obtained from the Morioka Branch, Fruit Tree Research Station, Japan, in May 1969, and "Gala", at the Department of Scientific and Industrial Research, New Zealand, in October 1969. The seeds obtained were utilized for sowing and raising seedlings at said Research Station, in April 1970, and resulting seedlings were then top-grafted on interstock "M.26", to accelerate the bearing, in 1974.

The present invention is directed to an apple tree "Kizashi", which is one individual from among 311 individuals derived from the cross between "Gala" (♀) (the seed parent) and "Fuji" (♂) (the pollen parent), and having an individual number "2660". The tree bore fruit in 1977, and attention was drawn to the excellent character of the fruit in 1978, and then the tree was selected as a favorable line in 1978. The trees, which have a line name "Ringo Morioka 41", have been provided for local adaptability tests since 1981, and were thereafter examined to determine the various characteristics thereof, over a period of three years of from 1987 to 1990. As a result, it was found that, for example, fruit of the trees had the desired characteristics, such as coloring, quality, storability and yield, as an extremely early apple variety, and that the tree was distinguishable from the parent varieties, "Fuji" and "Gala", as well as a check variety "Tsugaru", which are closely related to the present variety. Accordingly, the breeders denominated this variety as "Kizashi", in accordance with this invention. The genus and species of the tree is "*Malus pumila*".

Of the varieties, "Tsugaru" is a variety generated from a cross between "Golden Delicious" and "not specified variety", and was allocated an increased area for growth in Japan.

The breeders asexually reproduced this new and distinct variety of apple tree "Kizashi", by top-grafting on rootstock "M.26", at a number of public Fruit Tree Research Stations, and confirmed the homogeneity and stability of "Kizashi" according to this invention.

An application for this new variety of apple tree "Kizashi" was filed under the Seeds and Seedlings Law of Japan on Mar. 31, 1990, under the filing number 3826. The variety was registered on Dec. 16, 1991 under the number 2933.

SUMMARY OF THE VARIETY

This new variety of apple tree is genetically vigorous and moderately spreading. The tree has a rounded triangular shape and medium branching density, with scaffold branches about 70 degrees relative to the trunk. The occurrence of shoot and formation of spur are both good and productive with a regular crop. Although it is characterized in that the branch, three or more years old, shows a rough bark, internal necrosis has not been observed in the bark.

The shape of a leaf of the tree is long and narrow and lanceolate, and thus the leaf is a particular type of the apple variety.

In Iwate prefecture, Japan, the trees have the same flowering time as "Tsugaru" and "Fuji", i.e., in mid-May. The ripening of the present fruit occurs in mid-to late August at Morioka, and is earlier by 20 to 30 days than that of "Tsugaru" and "Gala". The size of the fruit averages about 200 g, and is slightly small, and the shape of the fruit is conical to rounded conical. The type of over color of skin of the fruit is deep red, corresponding to "deep red" in ISCC - NBS System to deep reddish brown (JHSC0708) corresponding to "deep reddish orange" in ISCC - NBS System, and it has a good appearance.

The flesh of the present fruit contains about 13% Brix, an abundance of malic acid (0.63 to 0.93%), and further, the flesh is rich in juice with a good texture and a moderately sweet with a pronounced level of subacidity. The keeping quality of the fruit is about one week, and this is medium as a very early apple variety.

There is no physiological fruit drop prior to picking of the fruit. Matured fruit left on the tree tend to be mealy. Although the tree has the same sensitivity as "Tsugaru" to scab, the tree has a slightly stronger resistance to Alternaria blotch than that of the check variety.

Compared with parent varieties, the shape of the fruit of the present variety is more rounded than that of "Gala", the seed parent, and the fruit does not have tendency to an inclination of the axis, as does "Fuji" the pollen parent.

The ripening of the fruit of the present variety is earlier by about 3 months than that of "Fuji".

Table 1 gives the cross compatibility between the new variety and other varieties.

TABLE 1

| Cross combination × | Number of flowers crossed | Number of fruits set | Percentage of fruits set |
|---|---|---|---|
| Kizashi × Fuji | 20 | 16 | 80.0 |
| Kizashi × Jonathan | 20 | 17 | 85.0 |
| Kizashi × Starking D. | 20 | 20 | 100.0 |
| Kizashi × Golden D. | 20 | 0 | 0 |
| Kizashi × Tsugaru | 20 | 17 | 85.0 |
| Fuji × Kizashi | 20 | 18 | 90.0 |
| Jonathan × Kizashi | 20 | 18 | 90.0 |
| Starking D. × Kizashi | 20 | 19 | 95.0 |
| Golden D. × Kizashi | 20 | 0 | 0 |
| Tsugaru × Kizashi | 20 | 20 | 100.0 |

The color description herein is from according to the Japanese Horticultural Plant Standard Color Chart (JHSC), with cross-reference to the ISCC - NBS System.

DESCRIPTION OF THE VARIETY

Figure 1:
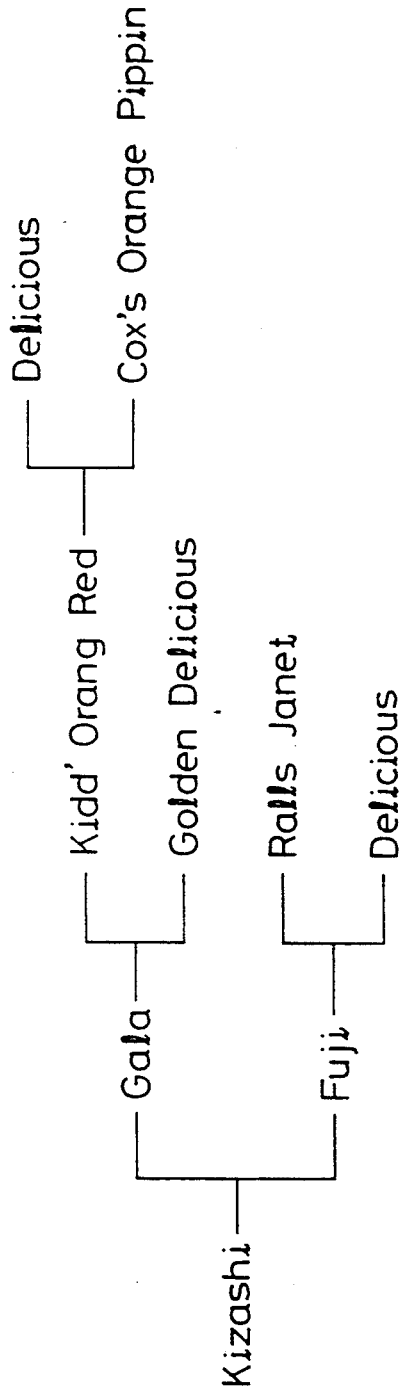
FIG. 1 gives the pedigree of the new and distinct variety of the apple tree "Kizashi"
Figure 2:
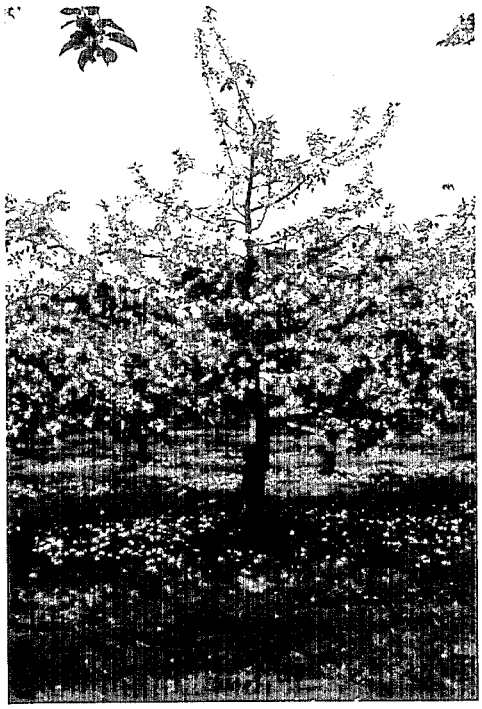
FIG. 2 is a photograph of a shape of the new variety of apple tree.
Figure 3:
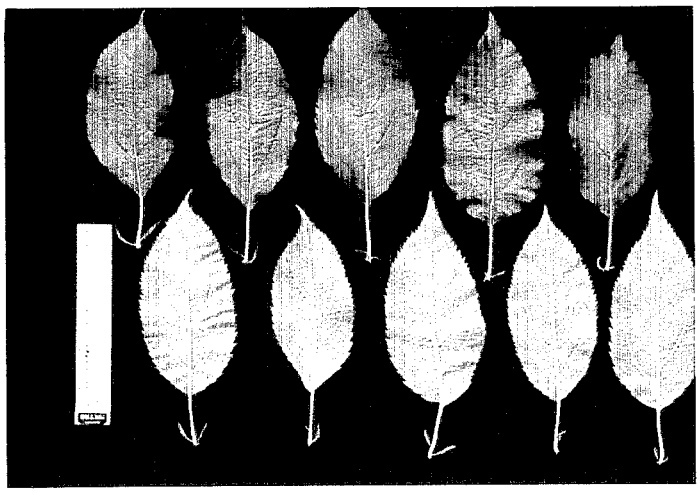
FIG. 3 is a photograph of adult leaves (upper and reverse side) of the new variety of apple tree.
Figure 4:
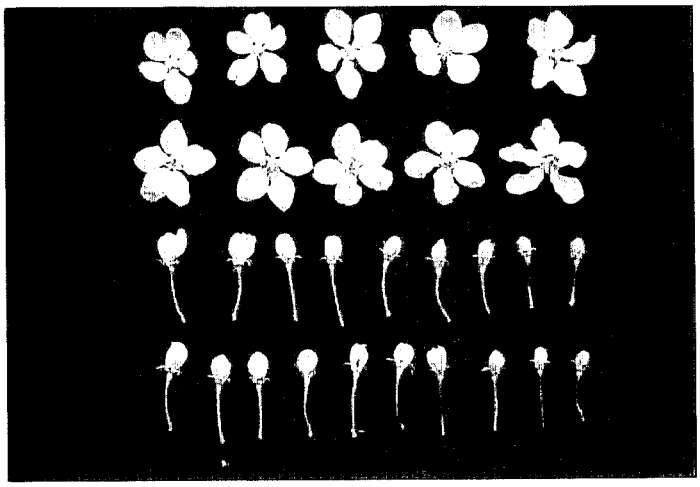
FIG. 4 is a photograph of the flowers of the new variety of apple tree.
Figure 5:
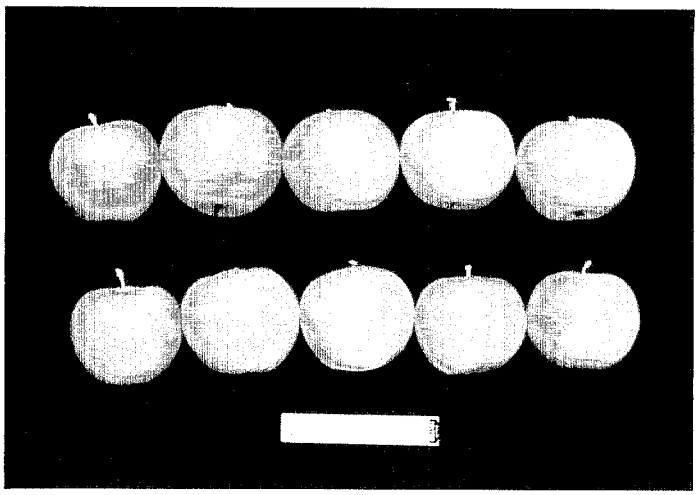
FIG. 5 is a photograph of side views of the fruit of the new variety of apple tree.
Figure 6:
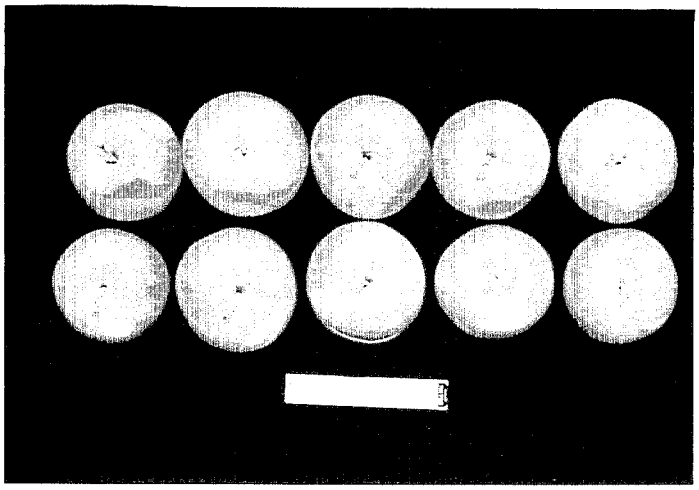
FIG. 6 is a photograph of cavities of the fruit of the new variety of apple tree.
Figure 7:
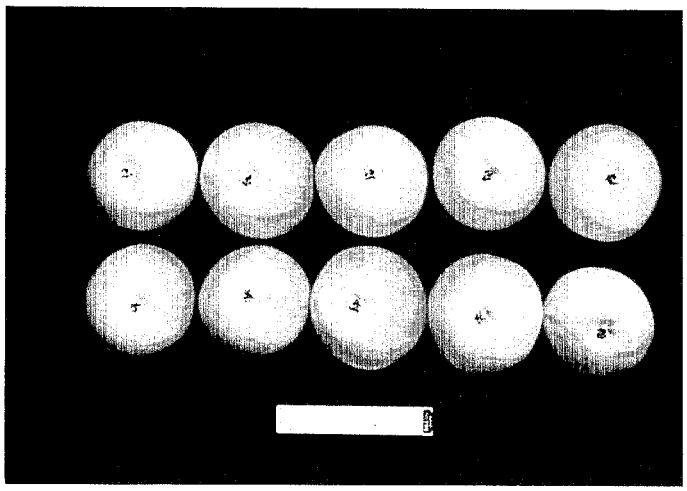
FIG. 7 is a photograph of basins of the fruit of the new variety of apple tree.
Figure 8:
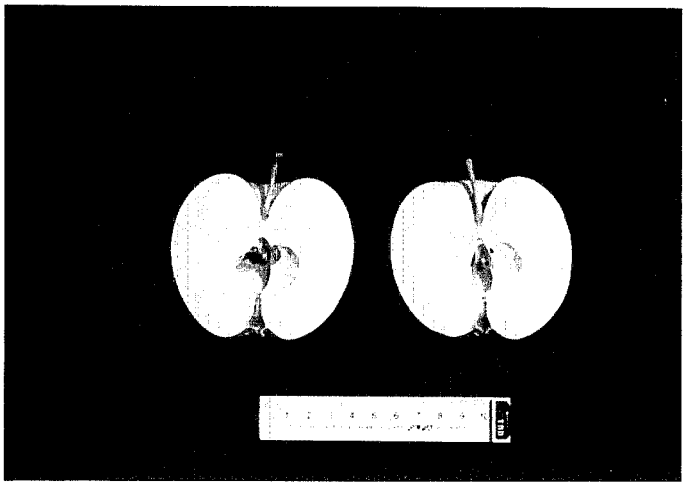
FIG. 8 is a photograph of longitudinal-sectional views of the fruit of the new variety of apple tree.
Figure 9:
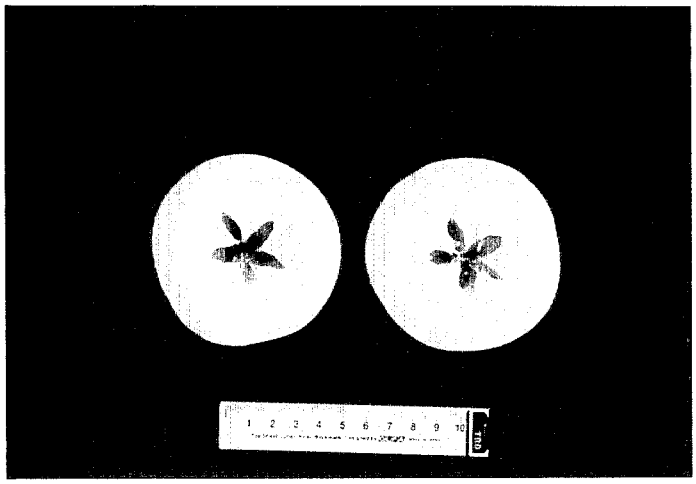
FIG. 9 is a photograph of cross-sectional views of the fruit of the new variety of apple tree.

The characteristics of the new and distinct variety of apple tree "Kizashi" are as follows:

Ploidy: Diploid

Tree:

*Habit of branches.*—Medium, slightly stronger degree of uprightness than "Tsugaru" and "Sansa".

*Angle between scaffold branch and trunk.*—About 70°.

*Size.*—Large, Larger than "Tsugaru" and fairly larger than "Sansa". Height 5 m, width 5.4 m, for 7-year-old tree on semi-vigorous rootstock, *M. prunifolia*, in Iwate prefecture of Japan.

*Vigor.*—Strong. Terminal shoot growth of scaffold branches about 49 cm.

*Thickness (one-year-old shoot).*—Medium.

*Length of internode (one-year-old shoot).*—Medium (3.4 cm).

*Number of spurs (per meter).*—Fairly many (10 to 11).

*Size of lenticels (one-year-old shoot).*—Medium, long-ellipse compared to roundness of "Tsugaru".

*Number of lenticels (one-year-old shoot).*—Much (numerous), same as "Tsugaru".

*Color of bark (one-year-old shoot).*—Dark reddish brown (ISCC - NBS).

*Pubescence of shoot.*—Weak.

*Predominance of bearing.*—On spur.
*Predominance of axillary flower bud.*—Few, very few compared to "Tsugaru" and "Sansa".

Leaf:
*Shape of leaf blade.*—Elongated, particularly long and narrow (lanceolate).
*Serrations of leaf edge.*—Serrated.
*Size of leaf (length).*—Long (length 12.1 cm, wide 5.8 cm).
*Color of leaf.*—Top surface dark green, bottom surface pale green, petiole pale yellow green, vein pale yellow green (all in ISCC - NBS System).
*Shape of stipules.*—Elongated, long and narrow.
*Size of stipules.*—Large.
*Length of stipules.*—Medium (2.9 cm).
*Thickness of petiole.*—Medium.

Flowers:
*Number of flowers (per cluster).*—Medium (4 to 6).
*Size (open flower).*—Medium.
*Color (unopen flower).*—White (JHSC0401, corresponding to "pink" in ISCC - NBS System).
*Shape of petal.*—Ovoid.
*Number of petals.*—Medium (5).
*Number of stamens.*—Medium.
*Color of anthers.*—Light yellow (JHSC2511).
*Amount of pollen.*—Large.
*Cross compatibility.*—Shown in Table 1.

Fruit:
*Shape.*—Round.
*Crowning at eye end.*—Weak.
*Aperture of eye.*—Open.
*Depth of basin (eye end).*—Shallow.
*Breadth of basin (eye end).*—Narrow.
*Depth of stem cavity.*—Medium.
*Breadth of stem.*—Medium.
*Size.*—Small (about 205 g, height 67 mm, diameter 80 mm when moderately thinned).
*Type of ground color.*—Light yellow green when ripe for picking, light yellow green to light yellow after extended storage (all in ISCC - NBS System).
*Type of over color of skin.*—Deep red to deep reddish orange when ripe for picking, deep red to deep reddish brown after extended storage (all in ISCC - NBS System).
*Intensity of over color.*—Deep.
*Form of over color of skin.*—Faint stripes to a uniform blush of substantially solid red (ISCC - NBS).
*Amount of over color of skin (percent of surface covered by red).*—Large (30 to 100%).
*Position of russet.*—On cheeks.
*Amount of russet.*—Slight.
*Raised russet lenticels.*—Present.
*Size of lenticels.*—Medium.
*Number of lenticels.*—Medium.
*Silvery mottle of skin (scarfskin).*—Present.
*Shininess of skin.*—Medium.
*Greasiness of skin.*—Weak.
*Bloom of skin.*—Present.
*Cracking tendency of skin.*—None.
*Surface texture of skin.*—Moderate.
*Length of stem.*—Medium (2.9 cm).
*Distinct swelling at end of stem.*—None.
*Shape of core.*—Conical.
*Size of core.*—Medium (5 core cells).
*Aperture of locules.*—Open.
*Color of flesh.*—White (JHSC2502), corresponding to yellowish white in ISCC - NBS System.
*Easy bruising of flesh.*—Medium.
*Browning of flesh.*—Weak.
*Firmness of flesh.*—Medium.
*Texture of flesh.*—Fine.
*Water core.*—None or weak.
*Sweetness of flesh.*—Medium (Brix 12.3°).
*Acidity of flesh.*—Strong (0.8%).
*Astringency of flesh.*—None.
*Flavor of flesh.*—Weak.
*Juiciness of flesh.*—Juicy.

Seed:
*Number of fully developed seeds.*—Many (8 to 10).
*Shape.*—Ovovoid.
*Size.*—Medium.

Physiological and ecological characteristics:
*Date of bud break.*—Medium (April 13th in Morioka prefecture, Japan).
*Season of flowering.*—Medium (May 15th, in Morioka prefecture, Japan).
*Season of leaf fall.*—Medium.
*Time fruit are ripe for eating.*—Early (August 14 to 29th, in Iwate prefecture, Japan).
*Predominancy of precocity.*—Medium.
*Self-fruitfulness.*—Weak.
*Early dropping of fruit.*—None or slight.
*Preharvest dropping of fruit.*—None or slight.
*Physiological disorder of fruit.*—Little.
*Keeping quality of fruit (normal storage).*—Short (5 days).
*Keeping quality of fruit (cold storage).*—Short (15 to 20 days).
*Occurrence of heart rot (core rot).*—None or weak.
*Resistance to Alternaria blotch.*—Moderate; same resistance as "Fuji".
*Resistance to powdery mildew.*—Moderate.
*Resistance to rough bark disorder.*—Moderate; same sensitivity as "Tsugaru" to scab.
*Resistance to aphids.*—Moderate.
*Cold resistance of trees.*—Moderate.

It is claimed:

1. A new and distinct variety of apple tree, substantially as illustrated and described herein, characterized over known apple trees by (A) having a strong vigor, and (B) having leaves which are a particular long and narrow shape, and (C) bearing slightly small, conical to rounded-conical, attractive brightly colored a deep red to deep reddish orange (ISCC - NBS) colored fruit, (1) maturing earlier than "Tsugaru", and (2) having a yellowish white (ISCC - NBS) flesh that is juicy with a good texture and a moderately sweet and sour taste, and (D) having an excellent consumption quality, in particular, in mid-summer.

* * * * *

Pedigree of the 'Kizashi' apple